United States Patent [19]

Shields, Jr. et al.

[11] Patent Number: 5,759,167

[45] Date of Patent: Jun. 2, 1998

[54] PATELLA BUTTRESSING APPARATUS

[75] Inventors: Clarence L. Shields, Jr., Los Angeles; Richard E. Riehl, Santa Monica, both of Calif.

[73] Assignee: Weber Orthopedic, Inc., Valencia, Calif.

[21] Appl. No.: 753,115

[22] Filed: Nov. 20, 1996

[51] Int. Cl.$^6$ .......................................... A61F 5/00
[52] U.S. Cl. .......................................... 602/26; 602/62
[58] Field of Search .......................... 602/23, 26, 60–63; 128/856, 882, 892

[56] References Cited

U.S. PATENT DOCUMENTS

| | | | |
|---|---|---|---|
| 4,201,203 | 5/1980 | Applegate | 602/26 |
| 4,296,744 | 10/1981 | Palumbo . | |
| 4,425,912 | 1/1984 | Harper | 602/26 |
| 4,445,505 | 5/1984 | Labour et al. | 602/26 |
| 4,585,003 | 4/1986 | Meistrell . | |
| 4,700,406 | 10/1987 | Meistrell . | |
| 4,706,673 | 11/1987 | Meistrell . | |
| 4,765,318 | 8/1988 | Tranberg et al. | 602/26 |
| 4,805,620 | 2/1989 | Meistrell . | |
| 4,841,957 | 6/1989 | Wooten et al. | 128/882 X |
| 5,024,216 | 6/1991 | Shiono | 602/26 |
| 5,077,837 | 1/1992 | Meistrell . | |
| 5,277,697 | 1/1994 | France et al. | 602/26 X |
| 5,462,517 | 10/1995 | Mann | 602/26 |
| 5,613,943 | 3/1997 | Palumbo | 602/26 X |

FOREIGN PATENT DOCUMENTS

| | | | |
|---|---|---|---|
| 600218 | 6/1994 | European Pat. Off. | 602/26 |
| 16032 | of 1898 | United Kingdom . | |

*Primary Examiner*—Richard J. Apley
*Assistant Examiner*—Denise Pothier
*Attorney, Agent, or Firm*—William W. Haefliger

[57] ABSTRACT

The method of positioning the patella, as during knee movement, that includes providing a support wrap to extend about the knee, providing a first opening through the wrap to extend in registration with the patella; providing a buttress for biasing the patella, the buttress being apart from the support wrap, and positioning the buttress to locate the second opening in substantial registration with the first opening; and providing retainer flap means and attaching the flap means to the support wrap with the flap means extending over the buttress and holding the buttress in position biasing the patella.

19 Claims, 6 Drawing Sheets

5,759,167

PATELLA BUTTRESSING APPARATUS

BACKGROUND OF THE INVENTION

This invention relates generally to wrap-type equipment for lending support to the knee as during leg flexing, and more particularly concerns method and apparatus for buttressing the patella in an adjustable manner.

There is need for improved equipment of the type referred to, and which enables effective positioning of the patella via adjustable buttressing, and without exertion of excess pressure upon the outer face of the patella. Also there is need for equipment which will maintain such desired buttressing without diminution, over periods of time accompanied by knee flexing. Conventional taping of the knee does not secure desired results.

SUMMARY OF THE INVENTION

It is a major object of the invention to provide improved apparatus and method meeting the above need.

Basically, the method of the invention includes:

a) providing a support wrap to extend about the knee, and providing a first opening through the wrap to extend in registration with the patella, b) providing a buttress for biasing the patella, the buttress being apart from the support wrap, and extending at the periphery of a second opening, and positioning the buttress to locate the second opening in substantial registration with the first opening, c) and providing retainer flap means and attaching said flap means to the support wrap with the flap means extending over the buttress and holding the buttress in position biasing the patella.

As will appear, the buttress is typically provided to have U-shape, and may be shifted in multiple modes of movement relative to the support wrap to an adjusted position, prior to application of the retainer flap means. Such multiple modes of movement may include rotation to orient the buttress relative to the opening in the support wrap, enabling desired edge buttressing of the patella after the retainer flap means is applied. In this regard, the opening in the support wrap and the opening defined by the U-shaped buttress are in registration with the patella to prevent undue pressure exertion directly onto the patella outer face, that would result in pain. Further, the buttress is typically provided to have an elastomeric ridge protruding toward edge extent of the patella, to comfortably bias the patella, edgewise. Also, the buttress is typically shifted or positioned relative to the applied support wrap, to at least in part overlap portions of said support wrap adjacent said opening.

It is another object to provide the support wrap and the retainer flap means to be stretchable, for clamping the buttress toward the patella, and also to stretch in the same direction during application of the wrap apparatus, so that the buttress opening and the opening through the support wrap are not misaligned. Both the support wrap and retainer flap may have intermediate hook and pile attachment elements located as will be seen to enhance buttress positioning and to assure retention of the wrap in selected position during knee flexing.

It is a further object of the invention to provide the support wrap to be stretchable and to have two wrappable legs protruding from a body portion, and to provide the retainer flap means to be stretchable and to have two wrappable legs protruding from a body portion that is connected to the support wrap body portion. All the legs are wrapped in the same clockwise (or counterclockwise) direction, during application of apparatus, to accommodate to the buttress in any selected position, and to obtain optimum patella buttressing and positioning.

Apparatus incorporating the invention comprises:

a) a support wrap to extend about the knee, and a first opening through the wrap to extend in registration with the patella, b) a buttress for biasing the patella, the buttress being apart from the support wrap and extending up the periphery of a second opening, and the buttress second opening positioned in substantial registration with the wrap first opening, c) and retainer flap means attached to said support wrap with the flap means extending over the buttress and holding the buttress in position biasing the patella, and assuring retention of the wrap apparatus in selected position during knee flexing.

Two legs of the retainer flap means are locally attachable to the buttress at selected positions, and are relatively stretchable to provide a means for adjustably rotating the buttress relative to the legs of the support wrap along which the buttress is linearly slidable as the flap means legs are stretched during their connection to the support wrap.

These and other objects and advantages of the invention, as well as the details of an illustrative embodiment, will be more fully understood from the following specification and drawings, in which:

DRAWING DESCRIPTION

FIG. 4 is a section like FIG. 3, showing clockwise application of the flap means over the knee area, to retain the buttress in patella biasing adjustment position;

Figure 1:
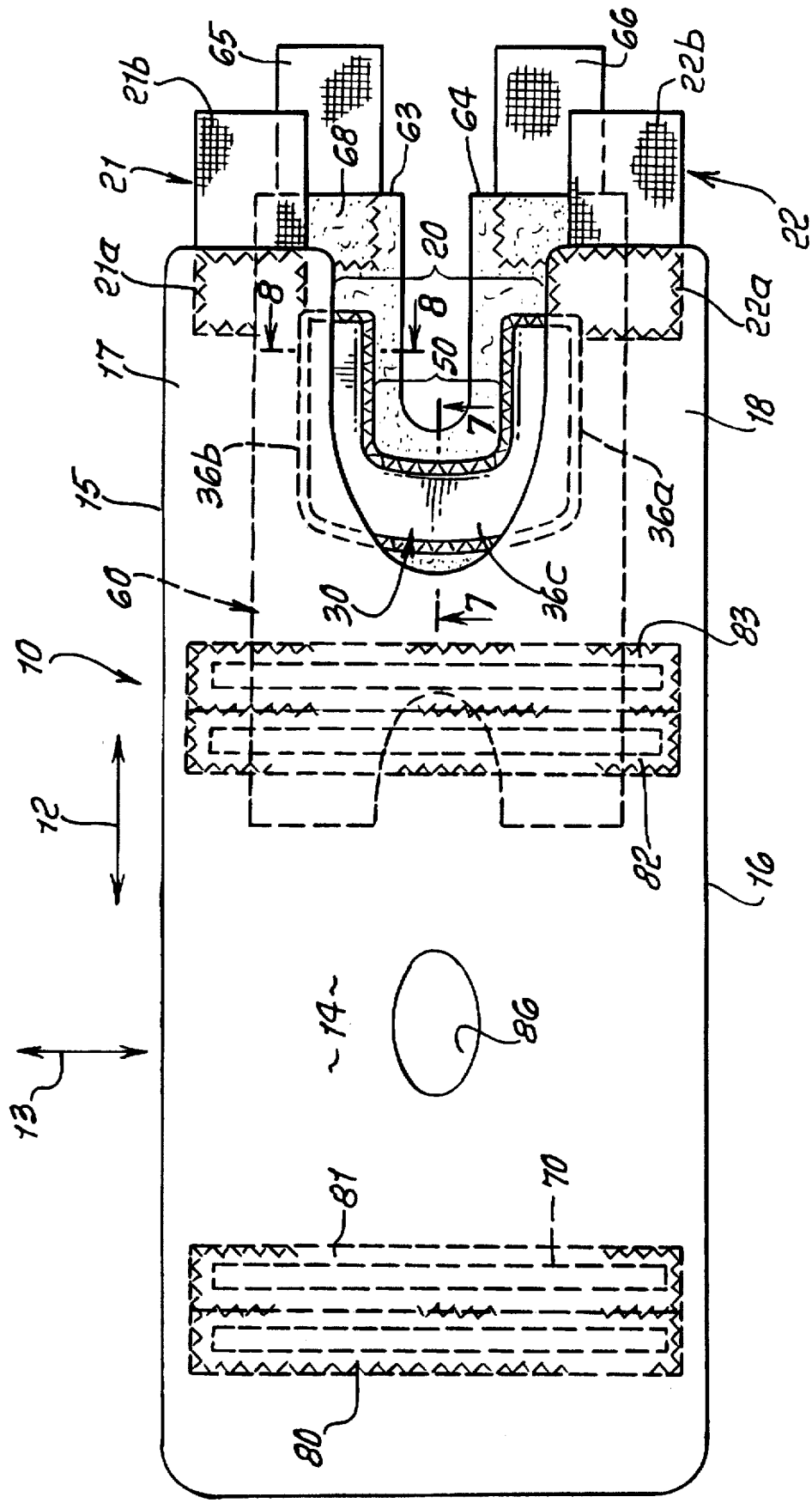
FIG. 1 is a plan view of the inner side of the support wrap; prior to its application to a knee.
Figure 6:
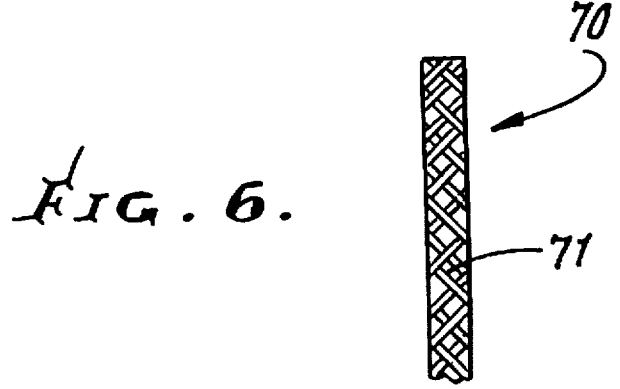
Figure 9:
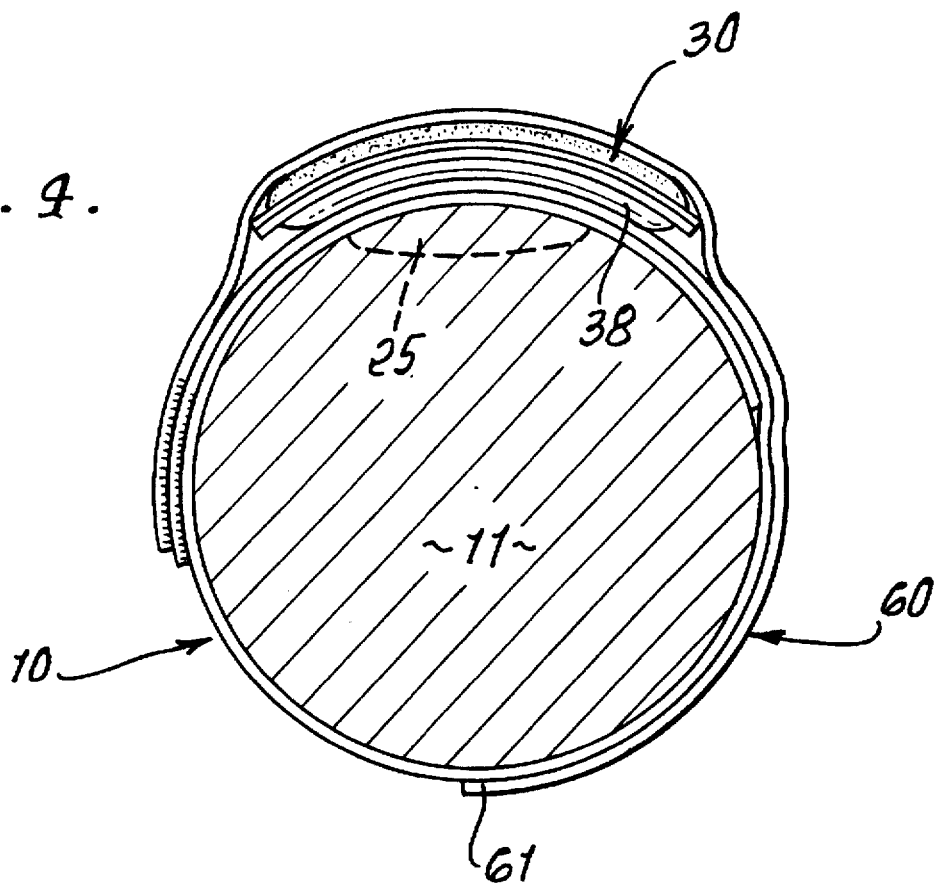
Figure 7:
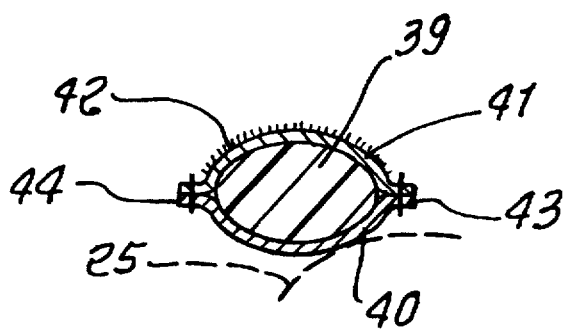

FIGS. 5(a)–(d) are plan views showing buttress maneuvering into different positions relative to a patella to be buttressed;

FIG. 6 is a plan view of a portion of a flat metallic spring;

FIG. 7 is an enlarged section taken on lines 7—7 of FIG. 1; and

Figure 8:
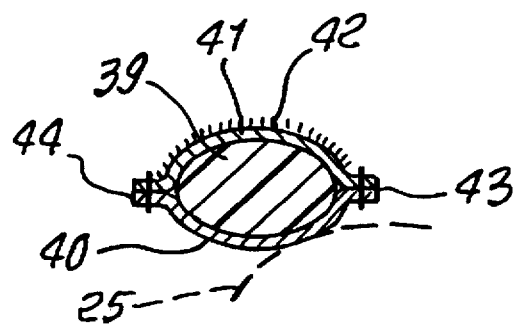
Figure 5A:
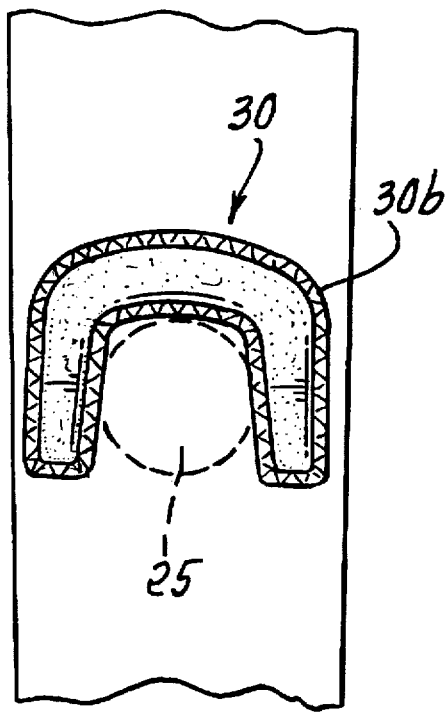
Figure 5B:
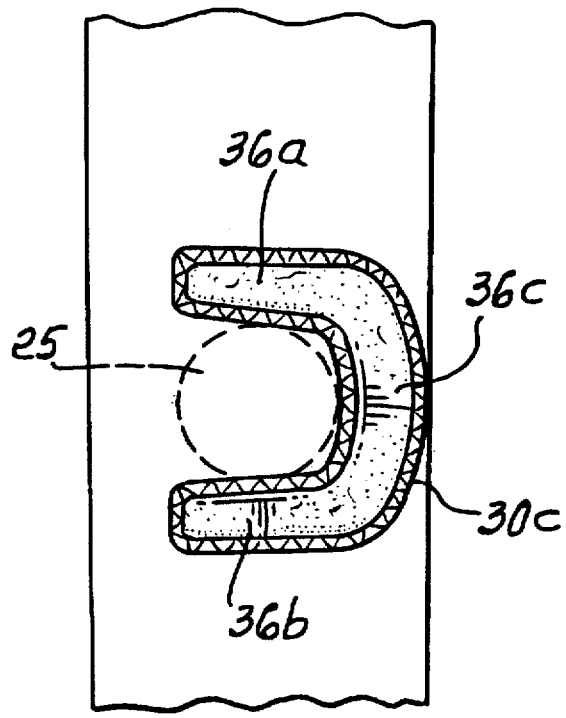
Figure 5C:
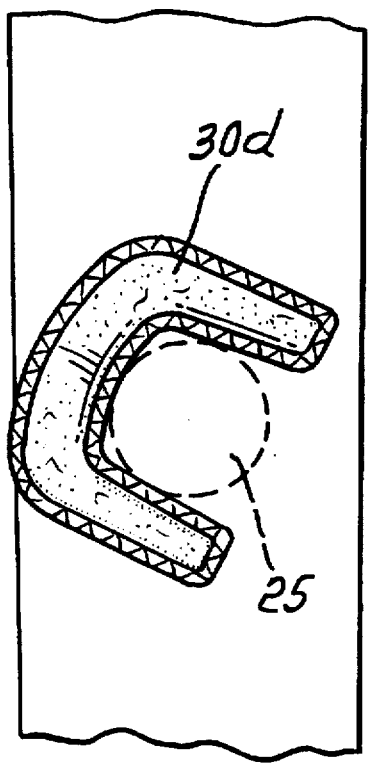
Figure 5D:
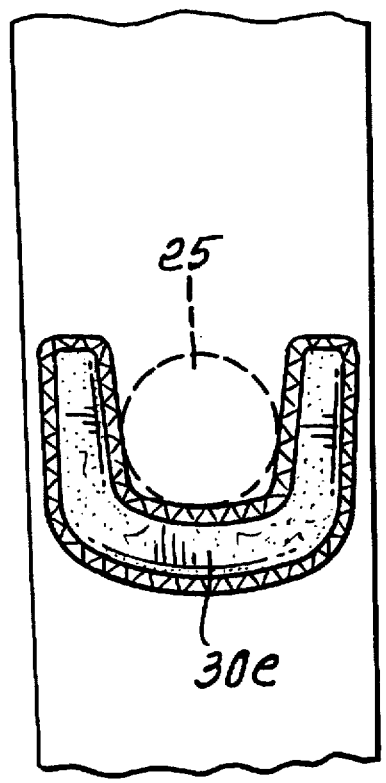

FIG. 8 is an enlarged section taken on lines 8—8 of FIG. 1.

DETAILED DESCRIPTION

Figure 2:
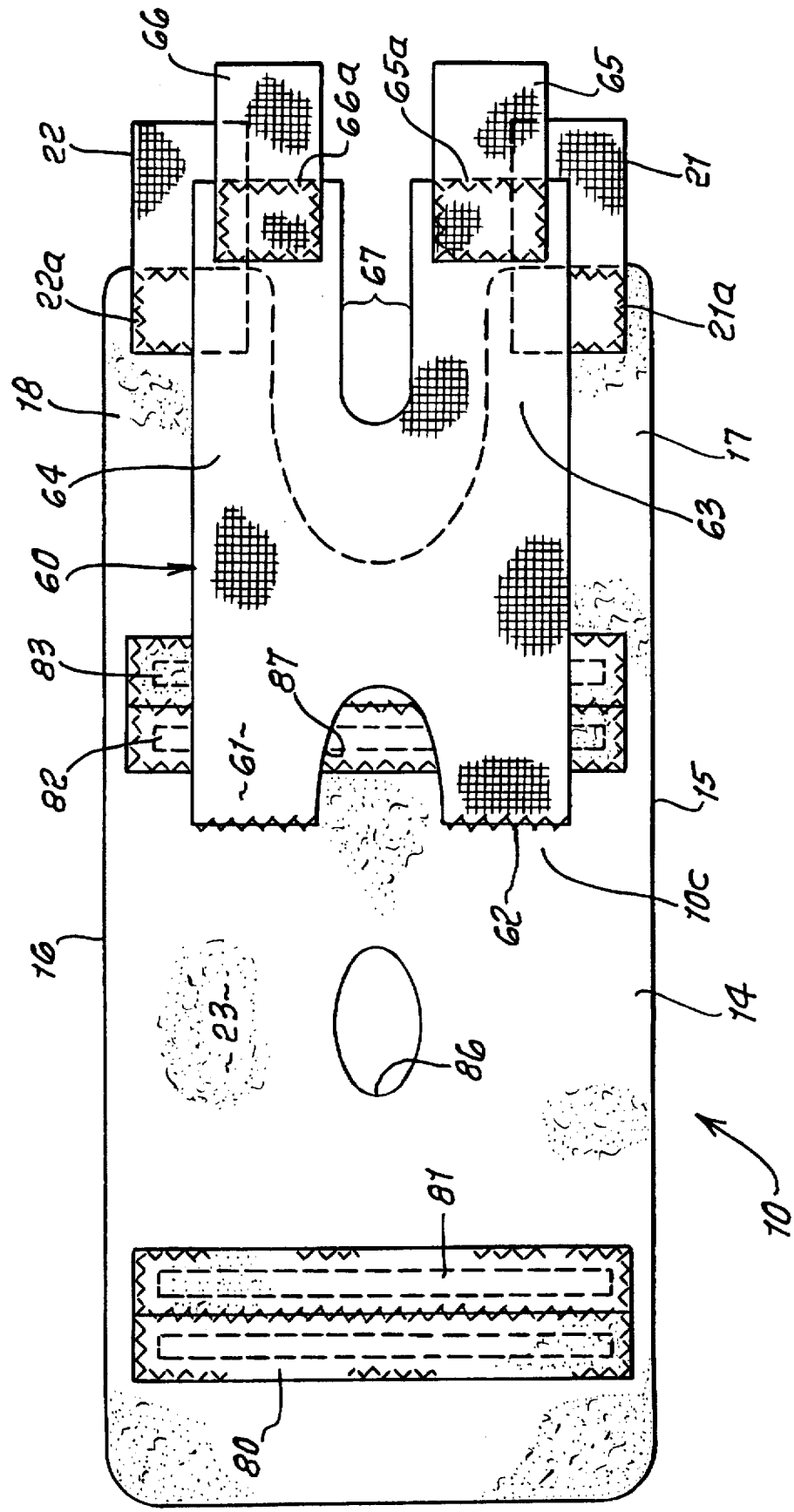
FIG. 2 is a plan view of the outer side of the support wrap, prior to its application to a knee, and which also shows the outer side of the retainer flap means.
Figure 3:
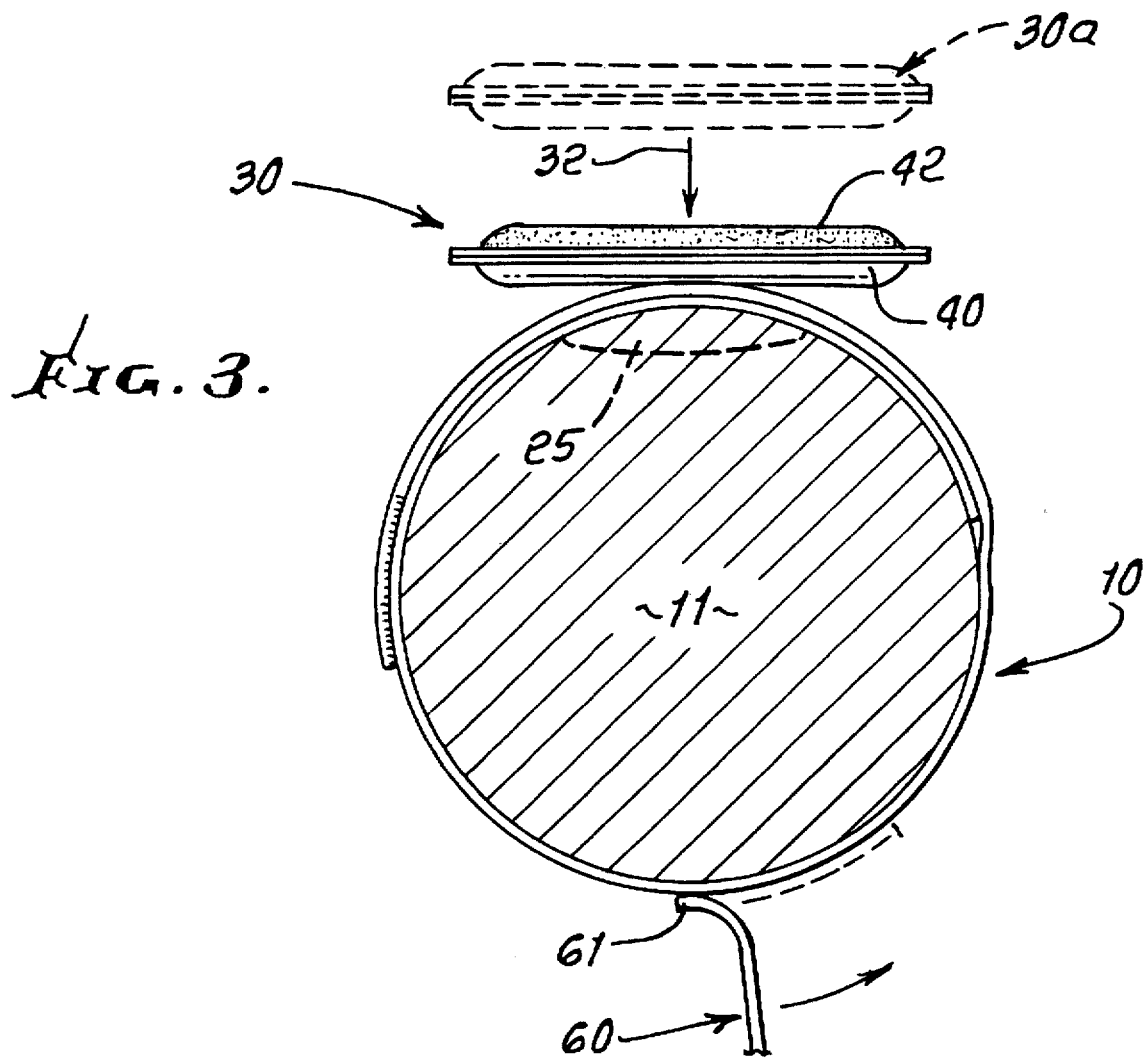
FIG. 3 is a section through a user's leg, showing clockwise application of the support wrap about the leg, under and over the knee areas; and also showing buttress maneuvering.

As shown in FIG. 1, a thin support wrap 10 is shaped to be wrapped about the knee 11, as shown in FIG. 3. The support wrap consists of material such as neoprene that is stretchable longitudinally, in the directions of arrows 12, and may also be stretchable laterally in directions 13. The support wrap has a body portion 14 located between laterally spaced longitudinally extending edges 15 and 16. Two legs 17 and 18 extend rightwardly from the body portion, and are laterally separated by a gap 20 as shown. Such legs consist of the same material as the body portion 14, and are stretchable longitudinally. Connector tabs 21 and 22 project from the rightward ends of the two legs, and are attached to the legs, as by stitching indicated at 21a and 22a. Tabs 21 and 22 carry hook or pile material shown at 21b and 22b, to mesh into pile or hook material 23 covering the opposite side of the body portion 14, as shown in FIG. 2, whereby when the support wrap is wrapped about different size human legs, at the knee region, the tabs may be easily connected to the body portion, at selected local areas determined by knee or leg size, and the degree of lengthwise stretch imparted to the wrap 10 to secure it in position.

In this regard, the lengthwise elongated gap 20 assures provision of a first opening to be easily located in registration with the patella, indicated at 25, in FIGS. 3 and 4. The gap is sized to approximately encompass or span the patella, whereby stretch pressure exerted by the wrap legs is not directly imparted downwardly onto the patella. At the same time, edge regions of the patella are exposed to be buttressed, as described below.

A buttress 30 is also provided as an element separate and apart from the wrap 10, in that it may be selectively applied in any of a number of positions, downwardly toward the gap 20, and toward edge portions of the legs, after they have been wrapped about the knee, and connected to the body portion 14, as via the connector tabs, the wrap 10 being in stretched condition. Thus, the buttress does not interfere with stretching of the wrap legs to fit to the knee, during stretch application of the support wrap to the leg at the knee. See the initial position of the buttress indicated by broken lines 30a in FIG. 3, being applied downwardly to the position shown.

The buttress is applied, as indicated by arrow 32, toward the gap 20, and the edge overlap of the buttress with edge portions of the two legs 17 and 18 enables removable support of the buttress on the support wrap. Note in this regard that the buttress may be rotatably located relative to the patella 25 in a large number of positions, a few of which appear in FIG. 5, views (a)–(d), and through a wide range of at least about 180° about an axis normal to and intersecting gap or opening 20. Numeral 32 indicates one such axis. Note the different selected positions of the U-shaped buttress indicated at 30b, 30c, 30d and 30e. That adjustable positioning enables the buttress to be located in best selected buttressing position, edgewise of the patella, to constrain the patella from shifting relative to the wearer's leg, in an unwanted direction or direction of movement.

Note that the buttress preferably has U-shape, with legs 36a and 36b and a cross piece 36c, that will overlap edge extents of the support wrap legs adjacent the gap 20, in a large number of buttress positions, as shown in FIG. 5. Such overlap enables adjustable sliding support of the buttress on the wrap legs, with the downward protruding ridge-like elastomer extent 38 of the buttress positioned to comfortably press sidewardly or edgewise against selected edge zones of the patella 25. The U-shaped buttress may consist of a foam rubber core 39, a smooth lower fabric liner 40, slidable along legs 17 and 18 and an upper fabric layer 41 carrying hook or pile material 42. The fabric layer 41 and liner 40 may be stitched together at protruding inner edge locations 43 and protruding outer edge locations 44 providing a U-shaped ledge or ledges offering further slidable support for the buttress on the wrap legs 17 and 18. The U-shape of the buttress provides for a second opening or gap 50 that is to be aligned with the patella, via registration with the first gap or opening 20, as is clear from FIG. 1. Gap 50 is adapted to span, or substantially span, the patella.

Also provided is retainer flap means to be attached to the support wrap with the flap means extending over the buttress and holding the buttress in position biasing the patella. As shown, the retainer flap means 60 has a body end portion 61 attached at 62, as by stitching, to a medial portion 10c of the wrap 10. See FIG. 3, where flap means 60 typically hangs downwardly as wrap 10 is applied about the knee 11, and as the buttress is located, as described. Flap means 60 has rightwardly extending legs 63 and 64, as shown in FIG. 1 and FIG. 2, that terminate at connector tabs 65 and 66 stitch connected at 65a and 66a to the legs. A medial, narrow gap 67 is provided between legs 65 and 66. Thin flap 60 may also consist of neoprene.

FIG. 4 shows the retainer flap 60 extended about the knee and over the buttress and the wrap 10 near the buttress to forcibly hold the buttress in position, while at the same time enabling maintenance of clearance for the patella above its upper face, as enabled by the registered openings or gaps 20 and 50, over which the legs 63 and 64 of the flap means 60 extend. The buttress is compressed by stretch of flap means 60 in retained position, with lateral force transmitted by the buttress edgewise to the patella, holding it in position. The side of the flap means 60 facing toward the buttress and toward the wrap 10 is covered with pile or hook material 68, to connect to the hook or pile material 42 on the buttress, and also to connect to the pile or hook material 23 on the outer side of the wrap. Also, the tabs 65 and 66 are provided with pile or hook material that connects to material 23 on the wrap.

Accordingly, an easily applied, highly adjustable, comfortable, and highly effective patella buttressing assembly is provided, which retains its buttressing capability for long periods. And, as the retainer flap is applied on the buttress and stretched, the buttress is caused to slide along the legs 17 and 18 of the wrap 10, as the legs 63 and 64 are stretched in the same direction as legs 17 and 18, to precisely and accurately position the buttress, linearly and rotatably, according to the relative degrees of stretch of the legs 63 and 64. Slidability of the buttress along the legs of the support wrap is maintained.

FIG. 6 shows a flat spring 70, made up of articulated, interconnected metallic links 71, which is highly flexible, and tends to return to elongated configuration as shown. Such springs are suitably embedded in the wrap 10, as at locations 80, 81, 82 and 83, as shown in FIG. 1, to resist lateral folding of the body portion 14 of the wrap. Openings 86 and 87 through the wrap 10 and flap 60 provide for protruding of leg flesh folds during application of the wrap, for comfort. The apparatus as shown and described may be considered as a preferred form of the invention, other forms being usable.

We claim:

1. A method of positioning the patella, as during knee movement, that includes a) providing a support wrap to extend about the knee, and providing a first opening through the wrap to extend in registration with the patella, b) providing a buttress for biasing the patella, the buttress being apart from the support wrap, and positioning the buttress in substantial registration with said first opening, the buttress being selectively applied in any of a number of selected positions about the support wrap, the buttress provided to have U-shape, and buttress legs formed to have length allowing adjustability of the buttress throughout a range of at least 180° about an axis normal to and intersecting said first opening, c) and providing retainer flap means and attaching said flap means to said support wrap with the flap means extending over and being retained to the buttress and holding the buttress in position biasing the patella, d) the buttress being slidably movable on the support wrap to said selected positions.

2. The method of claim 1 wherein the buttress is provided to have an elastomeric ridge positioned to comfortably bias the patella, edgewise.

3. The method of claim 2 wherein the buttress is positioned to at least in part overlap portions of said support wrap adjacent said opening.

4. The method of claim 1 wherein said support wrap is provided to be stretchable.

5. The method of claim 4 wherein said retainer flap means is provided to be stretchable, and to be stretched when attached to said support wrap, for clamping said buttress toward the patella.

6. The method of claim 1 wherein said support wrap and said flap means are provided to have hook and pile attachment means.

7. The method of claim 6 wherein said support wrap has a side facing said flap means, and including the step of providing one of said hook and pile attachment means to extend at substantially the entirety of said wrap side facing said flap means.

8. The method of claim 1 which includes providing said support wrap to be stretchable and to have two wrappable legs protruding from a body portion, and providing said retainer flap means to be stretchable and to have two wrappable legs protruding from a body portion that is connected to the support wrap body portion.

9. The method of claim 8 including wrapping all of said legs in the same clockwise direction during said patella positioning.

10. Apparatus for controllably positioning the patella, as during knee movement, comprising in combination
  a) a support wrap to extend about the knee, and a first opening through the wrap to extend in registration with the patella,
  b) a buttress for biasing the patella, the buttress being apart from the support wrap, and the buttress providing a second opening positioned in substantial registration with said first opening, the buttress being selectively applied in any of a number of selected positions about the support wrap, the buttress provided to have U-shape, and buttress legs formed to have length allowing adjustability of the buttress throughout a range of at least 180° about an axis normal to and intersecting said first opening,
  c) and retainer flap means attached to said support wrap with the flap means extending and being retained to the buttress and holding the buttress in position biasing the patella,
  d) the buttress being slidably movable on the support wrap to said selected positions.

11. The combination of claim 10 wherein the buttress has an elastomeric ridge positioned to comfortably bias the patella, edgewise.

12. The combination of claim 11 wherein the buttress is positioned to at least in part overlap portions of said support wrap adjacent said first opening.

13. The combination of claim 10 wherein said support wrap is stretchable, and includes two wrappable legs protruding from a body portion.

14. The combination of claim 13 wherein said retainer flap means is stretchable and has hook and pile attachment to said support wrap, said retainer flap means including two wrappable legs protruding from a body portion that is connected to said support wrap body portion.

15. The combination of claim 14 wherein all of said legs extend and are wrapped in the same clockwise direction about the knee.

16. The combination of claim 14 wherein said retainer flap means two legs are locally attached to the buttress and are relatively stretchable to provide a means for adjustably rotating the buttress relative to the legs of the support wrap along which the buttress is linearly slidable as the flap means legs are stretched during their connection to the support wrap.

17. A method of positioning the patella, as during knee movement, that includes
  a) providing a support to extend about the knee, and providing a first opening through the support to extend in registration with the patella, providing a buttress for biasing the patella, and
  b) positioning the buttress in substantial registration with said first opening, the buttress being selectively applied in any of a number of selected positions about the support, the buttress provided to have substantially U-shape and with legs formed to allow adjustability of the buttress throughout a wide range of at least about 180° about an axis normal to and intersecting said first opening,
  c) and providing retainer flap means and attaching said flap means to said support with the flap means extending over the buttress and holding the buttress in position biasing the patella, the buttress being slidably movable on the support to said selected positions.

18. A method of positioning the patella, as during knee movement, that includes
  a) providing a support wrap to extend about the knee, and providing a first opening through the wrap to extend in registration with the patella,
  b) providing a buttress for biasing the patella, the buttress being apart from the support wrap, and positioning the buttress in substantial registration with said first opening, the buttress being selectively applied in any of a number of selected positions about the support wrap, the buttress provided to have U-shaped extent and buttress legs formed to have length allowing adjustability of the buttress throughout a range of angles relative to the patella, such that the buttress may be caused to exert biasing force on different selected portions of the patella,
  c) and providing retainer flap means and attaching said flap means to said support wrap with the flap means extending over and being retained to the buttress and holding the buttress in position biasing the patella,
  d) the buttress being slidably movable on the support wrap to said selected positions.

19. Apparatus for controllably positioning the patella, as during knee movement, comprising in combination
  a) a support wrap to extend about the knee, and a first opening through the wrap to extend in registration with the patella,
  b) a buttress for biasing the patella, the buttress being apart from the support wrap, and the buttress providing a second opening positioned in substantial registration with said first opening, the buttress being selectively applied in any of a number of selected positions about the support wrap, the buttress provided to have U-shaped extent and buttress legs formed to have length allowing adjustability of the buttress throughout a range of angles relative to the patella, such that the buttress may be caused to exert biasing force on different selected portions of the patella,
  c) and retainer flap means attached to said support wrap with the flap means extending and being retained to the buttress and holding the buttress in position biasing the patella,
  d) the buttress being slidably movable on the support wrap to said selected positions.

* * * * *